(12) United States Patent
Weck et al.

(10) Patent No.: US 9,415,003 B2
(45) Date of Patent: Aug. 16, 2016

(54) SKIN CARE METHOD AND KIT

(71) Applicants: David Weck, Miami Beach, FL (US); Clemente Omar Villar, Miramar, FL (US)

(72) Inventors: David Weck, Miami Beach, FL (US); Clemente Omar Villar, Miramar, FL (US)

(73) Assignee: LIFT LABORATORIES, INC., Miami, FL (US)

( * ) Notice: Subject to any disclaimer, the term of this patent is extended or adjusted under 35 U.S.C. 154(b) by 0 days.

(21) Appl. No.: 14/194,944

(22) Filed: Mar. 3, 2014

(65) Prior Publication Data

US 2015/0245989 A1 Sep. 3, 2015

(51) Int. Cl.

| | |
|---|---|
| A61K 35/407 | (2015.01) |
| A61K 36/88 | (2006.01) |
| A61K 8/97 | (2006.01) |
| A23L 1/00 | (2006.01) |
| A61Q 19/00 | (2006.01) |
| A61Q 19/10 | (2006.01) |

(52) U.S. Cl.
CPC ... A61K 8/97 (2013.01); A23L 1/00 (2013.01); A61Q 19/00 (2013.01); A61K 2800/92 (2013.01); A61Q 19/007 (2013.01); A61Q 19/10 (2013.01)

(58) Field of Classification Search
None
See application file for complete search history.

(56) References Cited

U.S. PATENT DOCUMENTS 5,200,218 A * 4/1993 Lasater ............... A23K 1/1853
426/549
5,897,865 A 4/1999 Nguyen
(Continued)

FOREIGN PATENT DOCUMENTS

| GB | 598241 | * 9/1943 |
| GB | 626089 | * 12/1946 |

OTHER PUBLICATIONS

Website document entitled "The Vegetarian Food Pyramid" from the Loma Linda University. 2008. 4 pages. Obtained from website www.llu.edu/llu/sph/nutrition.*

(Continued)

*Primary Examiner* — Chris R Tate
(74) *Attorney, Agent, or Firm* — The Concept Law Group, P.A.; Scott D. Smiley; Yongae Jun

(57) ABSTRACT

A skin care method and kit is disclosed that includes instructions for a dietary skin care regimen. The regimen includes a list of prohibited and allowed foods. The list of prohibited foods includes red meat, chocolate, eggs, confections, alcoholic beverages, shellfish, fried foods, and tomatoes. The list of allowed foods includes chicken, turkey, non-fried fish, vegetables, fruit other than a tomato, and olive oil as a salad dressing. The skin care kit further includes a compliance report including the list of prohibited and allowed foods with corresponding data input fields for each food in the list of prohibited and allowed foods. The user indicates an amount of each prohibited and allowed food item consumed by the user in the corresponding data input field. A compliance rating system is disclosed in which the total number of servings of prohibited and allowed foods consumed by the user determines the user's compliance level.

19 Claims, 2 Drawing Sheets

(56) References Cited

U.S. PATENT DOCUMENTS

| | | | | |
|---|---|---|---|---|
| 6,107,349 | A * | 8/2000 | Mantynen | A61K 31/00 424/776 |
| 8,109,875 | B2 | 2/2012 | Gizewski | |
| 2006/0024391 | A1 * | 2/2006 | Lak | A23L 1/3002 424/728 |
| 2007/0202215 | A1 * | 8/2007 | Lak | A23L 1/296 426/61 |
| 2007/0225195 | A1 * | 9/2007 | Saito | A61K 8/361 510/399 |
| 2011/0117180 | A1 * | 5/2011 | Yan | A23L 1/0029 424/450 |
| 2011/0229537 | A1 | 9/2011 | Matravers et al. | |
| 2013/0017988 | A1 * | 1/2013 | Nishina | C11D 17/02 510/470 |

OTHER PUBLICATIONS

Website document entitled "Nutrition and healthy eating" from the Mayo Clinic. May 7, 2013. 4 pages. Obtained from website www.mayoclinic.org/healthy-lifestyle/nutrition-and-healthy-eating/in-depth/dash.*

* cited by examiner

SKIN CARE METHOD AND KIT

FIELD OF THE INVENTION

The present invention relates generally to a method and kit for improving skin health and appearance, and more particularly relates to a skin care method and kit including a dietary supplement, cleansing cream, cleansing soap, and instructions for a dietary regimen.

BACKGROUND OF THE INVENTION

Skin disorders, diseases, and conditions affect millions of individuals of all ages. Besides being physically uncomfortable and/or painful, such skin disorders/conditions can greatly impact an individual's quality and enjoyment of life. Individuals who suffer from skin disorders can also, as a result, suffer from social rejection, low self-esteem, depression, and withdrawal of social or physical contact. These can, and often do, affect other areas of an individual's life, such as his or her personal relationships and career. Some careers are even directly dependent on physical appearance.

Yet, treatment for skin conditions is very difficult to apply with any certain success. It often involves a trial and error process of attempting various topical treatments, ingestion of various drug therapies, and/or other costly alternative treatments, such as artificial light therapies. This process can be very expensive, consume a great deal of time and effort, and still result in only partial to no success. Treatments that work with one individual may not work with another individual, and an individual can become immune to a treatment that previously produced some successful results. Moreover, for any one particular skin condition, there can be offered a countless variety of treatments, which can confuse consumers.

It has been put forth that skin conditions and disorders are largely affected by the skin's relationship to internal bodily functions and internal organs, which are largely affected by an individual's dietary and personal habits. Yet, traditional physician prescribed treatments for skin disorders typically focus on either drug therapies, or externally applied topical treatments. They do not typically focus on a particular dietary regimen, or lifestyle practices. One reason is that promoting a dietary, or other lifestyle change as a treatment for a skin disorder is not as profitable. Traditional western medicine is not focused on holistic treatments to health problems. Also, implementing and tracking dietary and other lifestyle changes is difficult. Many individuals find it very difficult to change their diets and are unsure as to exactly what type of diet could be effective to produce positive results with regards to their skin health.

Accordingly, many prior-art solutions treat skin disorders using only one or two types of treatments, which do not address other areas of an individual's life that are likely to affect the effectiveness of the treatment(s). For example, using a topical medication on a skin disorder may only address a superficial expression of an underlying internal dysfunction, which if the internal dysfunction is not addressed, the topical medication will only meet with partial, temporary, or no success. Also, many prior-art solutions do not address use of daily skin care items, such as facial washes, soaps, and the like that may be irritating, or otherwise distressing the individual's skin.

Some prior-art treatments have severe side effects. For example, one treatment for the skin disorder, psoriasis, which is marked by red, itchy, scaly patches of skin, can involve ingestion of drugs that cause liver damage and kidney damage, requiring regular physician-monitoring of blood cells and organ function during use. Other medications can cause severe birth defects if the individual is pregnant during use. Many drug treatments are only effective during use and individuals become immune after a prolonged period of use.

Therefore, a need exists to overcome the problems with the prior art as discussed above and that provides a low cost, holistic solution to treat skin conditions internally, as well as externally, in a singular package and that does not have severe side effects.

SUMMARY OF THE INVENTION

The invention provides a skin care method and kit that overcomes the hereinafore-mentioned disadvantages of the heretofore-known devices and methods of this general type and that provides instructions for a particular dietary and lifestyle regimen, a compliance report and compliance rating system, a dietary supplement, a cleansing cream, and a soap bar that provides a user with a complete unitary package for a skin care program that includes internal, as well as, external skin care and skin health promoting components.

With the foregoing and other objects in view, there is provided, in accordance with the invention, a skin care method including obtaining a skin care kit, having a dietary supplement with at least one ingredient that promotes skin health; a skin cleanser that promotes skin health; instructions for following a dietary skin care regimen including a list of prohibited food items and a list of allowed food items; and a skin care regimen compliance report including the list of prohibited and allowed food items and a corresponding data input field for each food item in the list of prohibited and allowed food items. The method further includes consuming a single serving of the dietary supplement each day; cleansing a user's skin using the skin cleanser each day; consuming only foods from the list of allowed food items, the list of allowed food items including: chicken, turkey, non-fried fish, a vegetable, a fruit other than a tomato, and salad dressing in a form of olive oil; and refraining from consuming foods from the list of prohibited food items, the list of prohibited food items including: red meat, chocolate, an egg, a confection, an alcoholic beverage, shellfish, a tomato, and a fried food item.

In accordance with another feature, the skin cleanser is at least one of a moisturizing cleansing cream and a soap bar.

In accordance with another feature, the method includes indicating an amount of each prohibited and allowed food item consumed by the user in the corresponding data input field of the skin care regimen compliance report.

In accordance with another feature, an embodiment of the present invention includes determining a level of compliance with the dietary skin care regimen, wherein a total number of servings of prohibited food items and allowed food items consumed by the user determines the user's level of compliance and the level of compliance is one of the group of: a high level, a moderate level, and a non-compliant level.

In accordance with yet another feature of the present invention, an embodiment of the present invention includes instructions for following a skin care lifestyle regimen and performing at least one of a plurality of lifestyle activities, the plurality of lifestyle activities including: drinking a predetermined amount of water each day, exercising a predetermined amount of time each day, and consuming meals prior to a predetermined time of the day.

In accordance with a further feature of the present invention, the plurality of lifestyle activities further includes: drinking forty-eight ounces of water each day, exercising thirty minutes each day, and consuming meals prior to 8 P.M.

In accordance with yet a further feature of the present invention, an embodiment of the present invention includes determining a level of compliance with the dietary and lifestyle skin care regimen, wherein a total number of serving of prohibited and allowed food items consumed by the user and a total amount of time in which the user performs the plurality of lifestyle activities determines the user's level of compliance and the level of compliance is one of the group of: a high level, a moderate level, and a non-compliant level.

In accordance with a further feature of the present invention, the skin care regimen compliance report is configured to be displayed on a computer display and configured to allow the user to input data into the data input fields via a user input device.

In accordance with another feature, the dietary supplement further includes thiamin, riboflavin, niacin, vitamin B6, vitamin B12, and pantothenic acid.

In accordance with yet another feature of the present invention, the dietary supplement further includes at least one ingredient that promotes liver health.

In accordance with a further feature of the present invention, the at least one ingredient that promotes liver health is inositol.

In accordance with another feature of the present invention, an embodiment of the present invention further includes at least one moisturizing cleanser.

In accordance with another feature of the present invention, the skin cleanser includes a soap bar comprising chamomile.

In accordance with yet another feature of the present invention, the soap bar further comprises aloe vera.

In accordance with a further feature of the present invention, the skin cleanser further includes coconut oil.

In accordance with yet another feature of the present invention, the skin care kit further includes a coaching subscription form that allows the user to obtain a subscription that gives the user access to a care center for a period of time, the care center including at least one operator trained to answer questions about the dietary skin care regimen.

In accordance with another feature of the present invention, the method includes accessing a care center operator by one of calling the care center and logging on to the care center website.

In accordance with the present invention, an embodiment of the present invention includes a method for promoting skin care health and improving the appearance of skin affected by certain skin disorders, where the method includes obtaining a skin care kit comprising a dietary supplement including at least one ingredient that promotes skin health; a moisturizing cleansing cream; and a soap bar comprising chamomile. The skin care kit further includes instructions for following a dietary skin care regimen including instructions to not consume a food item from a list of prohibited food items, the list of prohibited food items including: red meat; chocolate; an egg; a confection; an alcoholic beverage; shellfish; and a tomato; and instructions to consume foods from a list of allowed food items, the list of allowed food items including: chicken; turkey; non-fried fish; a vegetable; a fruit other than a tomato; and salad dressing in the form of olive oil. The skin care kit further includes a skin care regimen compliance report including the list of prohibited and allowed food items and a corresponding data input field for each food item in the list of prohibited and allowed food items, and instructions for completing the skin care regimen compliance report including instructions to indicate an amount of each prohibited and allowed food item consumed by the user in the corresponding data input field. The user reads and follows instructions for the dietary skin care regimen. The user consumes a single serving of the dietary supplement each day the dietary skin care regimen is followed and the user cleanses the user's skin using the cleansing cream and soap bar each day the dietary skin care regimen is followed. The user also reads and follows instructions for completing the skin care regimen compliance report.

In accordance with another feature, an embodiment of the present invention also includes inputting data into data input fields via a user input device.

In accordance with yet another feature, the skin care regimen compliance report is configured to be displayed on a computer display.

Although the invention is illustrated and described herein as embodied in a skin care method and kit, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
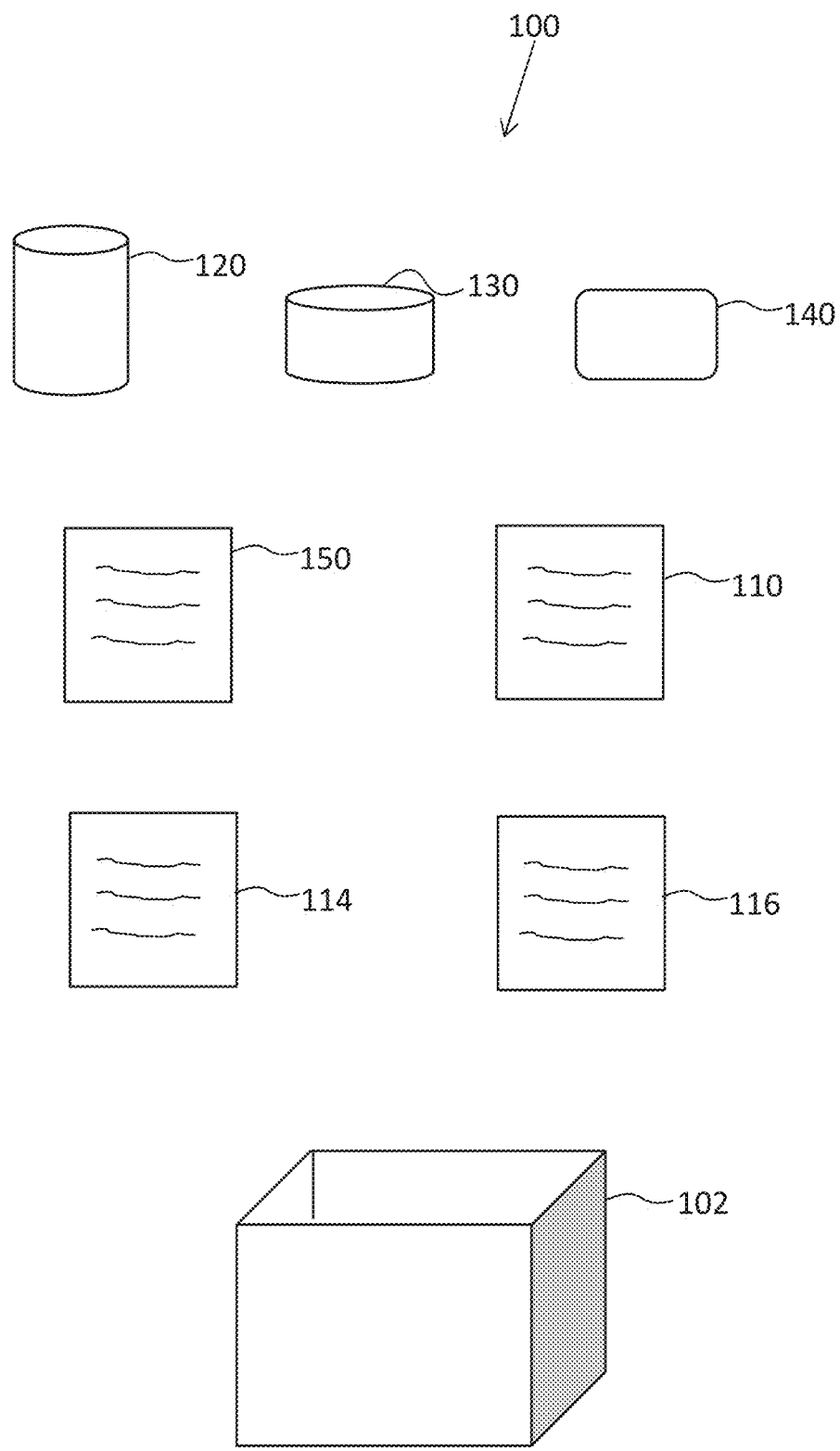
FIG. 1 is a schematic view of an exemplary skin care kit in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient method and kit for providing a skin care regimen that addresses a multitude of areas affecting a user's skin health. Embodiments of the invention provide a skin care method and kit that includes instructions for following a dietary program and a lifestyle regimen that promotes skin health, a liver promoting supplement, a skin cleanser such as a moisturizing cleansing cream and a cleansing soap bar. In addition, embodiments of the invention provide a tool for accountability, including a daily compliance report and method of use.

Referring now to FIG. 1, one embodiment of the present invention is shown in a schematic view. FIG. 1 shows several advantageous features of the present invention, but, as will be described below, the invention can be provided in several shapes, sizes, combinations of features and components, and varying numbers and functions of the components. The first example of a skin care kit 100, as shown in FIG. 1, includes a container 102 housing instructions for following a dietary program 110, instructions for following a lifestyle regimen 114, a dietary supplement 120, a cleansing cream 130, a soap bar 140, and a compliance report 150.

Figure 2:
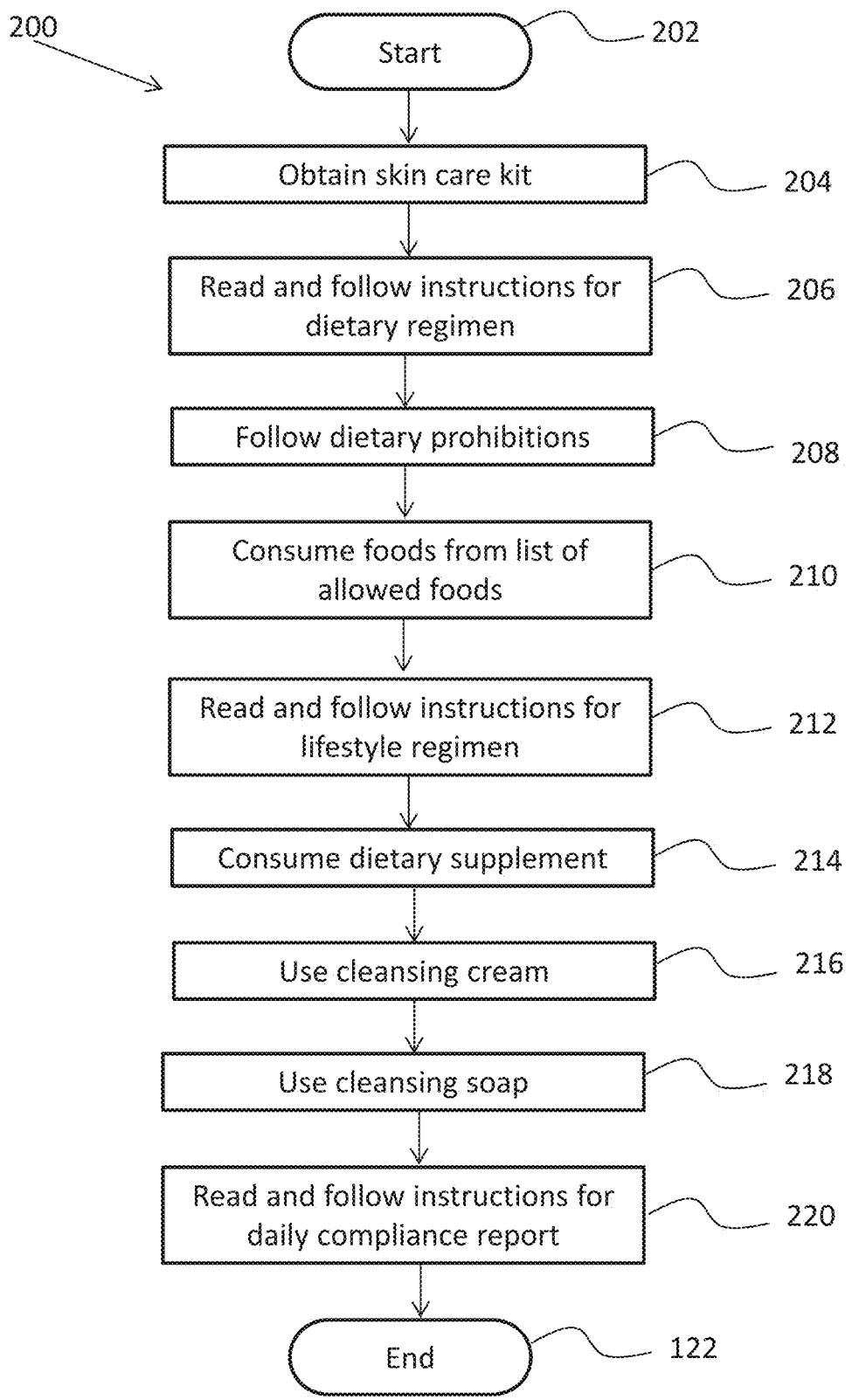
FIG. 2 is a flow diagram illustrating a process of using the skin care kit of FIG. 1.

The following figures will be described in conjunction with the process flow chart of FIG. 2. The process 200 of FIG. 2 begins at step 202 and moves directly to step 204, where the skin care kit 100 is provided to a user in a single container 102 housing all tangible elements of the kit 100. The container 102 can be a box, package, bag, and the like, sufficient to enclose and transport all tangible elements of the kit 100 in a single parcel. The exemplary elements included in the skin care kit 100 are depicted in FIG. 1 and will be described in more detail herein below.

In step 206, the user reads and follows instructions for following the dietary regimen 110. The instructions for the dietary regimen 110 can be provided in the form of a booklet, pamphlet, card, sheet, website page, software application, and the like. The instructions 110 can include a list of prohibited food items, which the user is advised not to consume, as well as a list of allowed food items, which the user is advised to consume. The list of prohibited food items preferably includes: red meat; chocolate; eggs; desserts, cakes, sweets, and other confections; alcoholic beverages; shellfish; a tomato; and a fried food. The user is advised not to consume any foods listed in the list of prohibited food items, including food items that may include merely a small portion of the prohibited food or include the prohibited food in a processed form. For example, the user is advised not to consume chocolate in any form, even as a single ingredient in a recipe including multiple ingredients. The user can be advised to refrain from consuming any food that contains eggs. The user is preferably advised to refrain from consuming tomato in any form, including a raw tomato, tomato juice, tomato sauce, ketchup, and the like. The user is also advised not to consume any food item that has been fried. In step 208, the user follows these dietary prohibitions by not consuming the food items listed in the list of prohibited food items.

The user is also advised to consume foods listed in the list of allowed food items. The list of allowed food items can include chicken; turkey; fish; vegetables; and fruit other than a tomato. The chicken and turkey meat is preferably from a low fat member, such as a chicken breast and a turkey breast, i.e., white meat. The instructions for allowed food items can also include instructions to consume salads, using only a light sprinkling of olive oil as salad dressing. In step 210, the user follows the dietary instructions 110 by consuming food items listed in the list of allowed food items. The inventor of the present invention has found that instructing users to refrain from consuming foods in the prohibited food items list, discussed above, as well as instructing users to consume from the allowed food items list provides a significant and relatively quick improvement in many troublesome skin conditions. In one embodiment, the dietary instructions 110 include instructions to only consume foods from the list of allowed food items. In another embodiment, the dietary instructions 110 include instructions to primarily consume food items from the list of allowed food items.

In step 212, the user reads and follows instructions for the skin care lifestyle regimen 114, which includes a plurality of lifestyle activities. The instructions for following the lifestyle regimen 114 include instructions for following lifestyle activities, which may be required to be performed each day or other period. These lifestyle activities include: 1) drinking a predetermined amount of water each day; 2) engaging in a predetermined number of bowel movements each day; 3) using a mild skin cleanser each day, such as the cleansing cream 130 and/or the soap bar 140; 4) consuming a single serving of the dietary supplement 120 each day; 5) sleeping a predetermined amount of hours per day; 6) exercising a predetermined amount of time per day, and 7) consuming meals prior to a predetermined time of day. In a preferred embodiment, the instructions 114 include advising users to drink eight eight-ounce glasses of water per day and engaging in at least one bowel movement per day. In another embodiment, the instructions 114 include sleeping at least eight hours per day. In yet another embodiment, the instructions 114 include exercising 30 minutes per day. In another embodiment, the instructions 114 include consuming meals prior to 8 P.M. The instructions for following the lifestyle regimen 114 further include instructions for lifestyle activities that the user is advised not to engage in. The list of prohibited activities can include: smoking and eating late in the evening (e.g., after 8 P.M.).

In step 214, the user consumes a single serving of the dietary supplement 120 provided in the skin care kit 100. The dietary supplement 120 includes a composition of ingredients that promote skin care health internally (as opposed to, for example, external topical medications), through consumption and ingestion of beneficial vitamins, minerals, herbs, and other ingredients, the ingredients preferably included in an amount that does not cause harmful side effects. Vitamins and minerals that can be provided in the supplement 120 include vitamin C, vitamin E, and selenium, which promotes healthy skin. The dietary supplement 120 can further include complex B vitamins, which are needed for healthy skin, as well as, proper liver function. Complex B vitamins are: thiamin (vitamin B1), riboflavin (vitamin B2), niacin (vitamin B3), vitamin B6, vitamin B12, and pantothenic acid (vitamin B5). The dietary supplement 120 preferably includes ingredients that promote liver health, as well. The dietary supplement 120 can further include choline bitartrate, di-methionine, desiccated liver-promoting concentrate, and inositol. Inositol is a naturally occurring carbocylic polyol that aids in preventing the collection of fats in the liver.

The dietary supplement 120 can be provided in a container, such as a bottle. The supplement 120 is of a consumable composition comprising one or more of the ingredients described above. The consumable composition can be provided in the form of, for example, a pill, a tablet, a capsule, and/or a powder or granules, with each serving of the consumable composition effective to promote skin health. The consumable composition is preferably provided in individual separate servings such that a single serving of the composition can be easily consumed daily by the user. One exemplary embodiment of the dietary supplement 120 in accordance with the present invention is a bottle of capsules, each capsule containing an effective amount of complex B vitamins, choline bitartrate, di-methionine, desiccated liver concentrate and inositol, with instructions to consume a single capsule each day.

The skin care kit 100 also includes an externally applied component regimen. Even if the user is provided with instructions for an internal component regimen that includes a dietary program 110 of prohibited foods and supplements that promote skin health, the user may still yet continue to use externally applied skin products that irritate or are otherwise harmful to the user's skin. Accordingly, the skin care kit 100 includes gentle, nourishing face and body skin cleansers, such as the exemplary cleansing cream 130 and soap bar 140.

In step 216, the user cleanses his or her skin with the cleansing cream 130. The cleansing cream 130 is preferably used by the user once in the morning and once in the evening, instead of the user's normal daily facial cleanser. The cleansing cream 130 can be applied to the user's face, massaged into the skin, and removed with a wash cloth and water. The cleansing cream 130 is preferably of a moisturizing cream that prevents dry skin conditions, such as, for example, dry scaly skin patches from psoriasis. The cleansing cream 130 is preferably devoid of skin irritants, such as irritating fragrances, dyes, and preservatives. The cleansing cream 130 can include a plurality of moisturizing oils, such as for example, coconut oil, sunflower oil, and sweet almond oil. Coconut oil prevents dry, flaking skin by improving the moisture and lipid content of the skin, nourishing skin tissue, eliminating dead skin cells, providing antibacterial properties, and soothing irritated skin. Sunflower oil includes a very high content of vitamins E, A, C and D, all of which have skin protective qualities. Almond oil is also moisturizing, having high vitamin E content, without being pore clogging. The cleansing cream 130 can be made in accordance with methods and apparatuses known in the art.

In step 218, the user cleanses his or her skin with the soap bar 140. The soap bar 140 is preferably used by the user at least once per day to cleanse the user's body, instead of the user's normal daily body cleanser. The soap bar 140 can be applied to the user's body, massaged into the skin, and rinsed with water. The soap bar 140 is preferably devoid of skin irritants, such as irritating fragrances, dyes, and preservatives. The soap bar 140 can include a plurality of moisturizing oils, such as for example, coconut oil, palm oil, canola oil, olive oil, and castor seed oil. The soap bar 140 preferably includes chamomile and aloe vera extract. Chamomile is soothing to the skin. Chamomile includes flavonoid and essential oils that possess significant anti-inflammatory properties. Aloe vera possesses healing and anti-bacterial properties. Aloe vera has amino acids, enzymes, proteins, vitamins, and minerals that nourish the skin. The soap bar 140 can be made in accordance with methods and apparatuses known in the art.

In step 220, the user reads and follows instructions for completing the skin care regimen compliance report 150. The user is preferably instructed to complete a single compliance report 150 each day. This provides the psychological benefit of reinforcing daily compliance and provides a measure of accountability to increase the likelihood of daily compliance by the user. It also allows the user to more accurately assess his or her compliance with the regimen using objective data. The term "compliance report," as used herein, is intended to indicate a printed document or software application that displays a list of features of the dietary and lifestyle regimen 110, 114 of the present invention to the user, with corresponding fields in which the user can input data regarding the user's compliance with each of the dietary and lifestyle regimen features 110, 114.

The compliance report 150 can be provided in the form of a booklet, pamphlet, card, sheet, website page, other software application interface, and the like. In an exemplary embodiment, as illustrated in FIG. 1, the compliance report 150 is provided as a single sheet of paper. The kit 100 preferably includes a multitude of compliance reports 150 that can be completed by the user each day. The sheet can include a pre-printed list of each of the features of the dietary and lifestyle regimen 110, 114 of the present invention and a corresponding compliance data field, such as fill-in bubbles, for each feature. One embodiment of the compliance report 150 can include an identification area in which the user can enter his or her name, the date of the report, and any other identifying information, such as a subject number, if the user is participating in a study.

The compliance report 150 can also include a list of each of the prohibited foods, a list of the allowed foods, and a list of required lifestyle activities. A plurality of fill-in bubbles can be provided beside each prohibited and allowed food item, wherein each successive fill-in bubble represents an increasing number of portions, or servings of the food item consumed by the user on the reporting day. In one embodiment, there can be provided five bubbles. The first bubble represents zero servings of the food item consumed. The second bubble represents one serving of the food item consumed. The third bubble represents two servings of the food item consumed. The fourth bubble represents three servings of the food item consumed. And the fifth bubble represents four or more servings of the food item consumed. The user is instructed to mark the bubble that indicates the number of servings of the prohibited or allowed food item consumed on the reporting day.

In a like manner, a plurality of fill-in-bubbles can be provided beside each lifestyle activity, wherein each successive fill-in bubble represents an increasing number of predetermined measurable increments of the lifestyle activity performed by the user on the reporting day. For example, the lifestyle activities can include: hours slept by the user, minutes of exercise, number of dietary supplement 120 servings consumed, and number of times the cleansing cream 130 is used.

In one embodiment of the present invention, a compliance rating feature is included to provide the user with objective criteria for assessing his or her compliance. The compliance rating feature can include instructions for determining a level of compliance with the dietary and lifestyle skin care regimen 110, 114. More specifically, a total number of serving of prohibited and allowed food items consumed by the user and a total amount of time in which the user performs the plurality of lifestyle activities determines the user's level of compliance. The compliance report 150 can include a compliance rating chart or table that provides a rating scheme for determining a high level of compliance, a moderate level of compliance, and non-compliance by the user. For example, if 0 to 6 servings of prohibited food items are consumed on the reporting day, the chart can indicate a high level of compliance. If 7 to 10 servings of prohibited food items are consumed on the reporting day, the chart can indicate a moderate compliance level. If more than 10 servings of prohibited food items are consumed on the reporting day, the chart can indicate non-compliance of the regimen by the user for the reporting day. In a similar manner, for allowed foods, the chart can indicate high, moderate, and no compliance ranges of servings of allowed foods consumed. For example, if 13 to 17 servings of allowed foods are consumed on the reporting day, the chart can indicate a high level of compliance. If 12 to 10 servings of allowed foods are consumed on the reporting day, the chart can indicate a moderate level of compliance. If less than 10 servings of allowed foods are consumed on the reporting day, the chart can indicate non-compliance of the regimen by the user for the reporting day. In a similar manner, for lifestyle activities, the chart can indicate high, moderate, and no compliance ranges of measurable increments of lifestyle activities performed by the user on the reporting day. For example, if the user's activities fall in the range of 32 to 51, the chart can indicate a high level of compliance. If the user's activities fall in the range of 31 to 26, the chart can indicate a moderate level of compliance. If the user's activities are less than 31, the chart can indicate non-compliance of the regimen by the user for the reporting day.

Instructions for completing the compliance report 150 can be provided in the form of a booklet, pamphlet, card, sheet, website page, software application, and the like. The instructions can provide a detailed explanation of how the user can complete the compliance report 150, what the compliance report 150 indicates or means, and how to determine the user's level of compliance in accordance with the compliance rating chart.

Although the compliance report 150 and the instructions for following the dietary and lifestyle regimens 110, 114 of the present invention have been described herein primarily as printed paper documents, the report and instructions can be implemented by a software application. The software application can include computer code stored in a memory and processed by a processor of a computer to be displayed on a computer display. In a software embodiment, for example, the instructions for following the dietary and lifestyle regimens 110, 114 can be displayed on a webpage, presented by a browser, on a display of the computer, such as a mobile electronic device or smartphone. Similarly, the compliance report 150 can be displayed on a computer display. The user can input compliance report data for a particular report day via a user computer input device, such as a keyboard, touchpad, mouse, and the like. The user input data is then stored in a memory, or in a database located at a server. In this manner, i.e., storing in a digital format accessible by a computer (as opposed to a paper format), compliance report data collected over a period of time can be more readily tracked and analyzed by the computer processor. The software may include instructions for analyzing collected compliance report data and displaying the analyzed data as a chart or graph on the display, showing, for example, changing levels of compliance over a period of time.

The following formulations are non-limiting examples of skin care compositions that are suitable for inclusion in the skin care method and kit of the present invention, as discussed above. While particular embodiments of the present invention have been described, it will be apparent to those skilled in the art that various changes and modifications to the exemplary embodiments can be made without departing from the spirit and scope of the invention. For example, one or more ingredients listed below may be omitted in some embodiments and one or more ingredients not listed below may be added in other embodiments.

TABLE 1

List of ingredients included in an exemplary embodiment of the dietary supplement 110

| Ingredient | Amount per serving (mg) |
|---|---|
| Thiamin (vitamin B1) | 3 |
| Riboflavin (vitamin B2) | 3 |
| Niacin | 10 |
| Vitamin B6 | 1.65 |
| Vitamin B12 | 2 |
| Pantothenic Acid | 2 |
| Choline Bitartrate | 240 |
| Di-Methionine | 110 |
| Desiccated Liver Concentrate | 86 |
| Inositol | 83 |

TABLE 2

List of ingredients included in an exemplary embodiment of the soap bar 140.
Ingredients

*Cocos Nucifera* (Coconut) Oil
*Elaeis Guineensis* (Palm) Oil
*Brassica Napus* Seed Oil
Canola Oil
*Olea Europaea* (Olive) Fruit Oil
*Ricinus Communis* (Castor) Seed Oil
Caprylic/Capric Triglyceride
*Aloe Barbadensis* Leaf Extract
*Chamomilla Recutita* (Chamomile) Flower Extract
Glycerin

TABLE 3

List of ingredients included in an exemplary embodiment of the cleansing cream 130
Ingredients

*Cocos Nucifera* (Coconut) Oil
Isopropyl Palmitate
*Helianthus Annuus* (Sunflower) Seed Oil
Cetearyl Alcohol
Glycerin
Glyceryl Stearate
Stearic Acid
Dimethicone
*Prunus Amygdalus Dulcis* (Sweet Almond) Oil
*Arnica Montana* Flower Extract
Phenoxyethanol
Caprylyl Glycol
Sorbic Acid
Carbomer
Sodium Hydroxide TABLE 3-continued List of ingredients included in an exemplary embodiment of the cleansing cream 130
Ingredients Disodium EDTA
*Lavendula Angustifolia* (Lavender) Flower/Leaf/Stem Extract
Tocopheryl Acetate
*Hedera Helix* (Ivy) Extract
*Aloe Barbadensis* Leaf Juice In one embodiment of the present invention, a coaching subscription form 116 is included in the skin care kit 100. The coaching subscription form 116 can be provided in the form of a booklet, pamphlet, card, sheet, website page, software application, and the like. In FIG. 1, the coaching subscription form 116 is formed as a sheet that the user can fill-in with information, such as a user name, a password, and user contact information. The user can submit the filled-out form in order to obtain a subscription that gives the user access to a care center for a period of time. The user may pay a predetermined amount in order to subscribe to care center access for the period of time. The care center can be a location within a physical building that houses a plurality of care center operators that are trained to answer questions regarding the dietary and lifestyle regimen. One of the drawbacks of following a dietary program that restricts the type of foods that may be consumed by the dieter is that the dieter may not be certain whether a particular food item is prohibited or allowed at any given moment. Accordingly, it is advantageous to provide a subscription to a care center service, in which users may call in at any time and receive advice about the dietary and lifestyle regimen, such as, whether a particular food item is allowed or prohibited. In another embodiment, the care center can be a website in which users can log-in and receive online advice by email correspondence or online, real-time advice from a care center operator through the website by, for example, a text-based and/or video-based chat room.

The skin care kit 100 provides several advantages over the current art. The ingredients and dietary and lifestyle regimens 110, 114 provided by the kit 100 include gentle, yet effective treatments for even the more severe skin conditions. In many cases, results are seen within 10 days of compliance and substantial improvements in the appearance of the troublesome skin condition can occur within a few months of compliance, without the need for costly and time consuming medical treatment. The compliance report 150, including the compliance rating chart, provides a tool for accountability and self-assessment to encourage and reinforce compliance with the dietary and lifestyle changes required to improve the user's skin health and appearance, which may be difficult to adhere to for some individuals. By providing a compliance rating system, users receive a psychological reinforcement to continue the beneficial skin improvement behaviors. Importantly, the skin care kit 100 provides both internal and external components within a singular package, container, or unit, which provides convenience for users that are bombarded with a myriad of potential skin care choices. By providing all of the internal and external components in the form of a kit 100 users can receive the psychological relief that everything they need is in one location.

A skin care method and kit has been disclosed that includes instructions for a dietary and lifestyle regimen that improves the appearance of skin disorders, when used in conjunction with a dietary supplement and cleansing products that promote skin health.

What is claimed is:

1. A skin care method comprising and steps of:
   obtaining, by a user, a skin care kit including:
      a dietary supplement comprising an effective amount of thiamine, riboflavin, niacin, vitamin B6, vitamin B12, pantothenic acid, choline bitartrate, di-methionine, desiccated liver concentrate, and inositol;
      a skin cleanser that promotes skin health; and
      instructions for following a dietary skin care regimen including a list of prohibited food items and a list of allowed food items, the list of prohibited food items including red meat, chocolate, an egg, a confection, an alcoholic beverage, shellfish, a tomato, and a fried food item;
   consuming, by the user, a single serving of the dietary supplement each day;
   cleansing, by the user, the user's skin with the skin cleanser each day; and
   consuming, by the user, only foods from the list of allowed food items, the list of allowed food items including:
      chicken;
      turkey;
      non-fried fish;
      a vegetable;
      a fruit other than a tomato; and
      salad dressing in a form of olive oil.

2. The skin care method according to claim 1, wherein the skin cleanser is at least one of a moisturizing cleansing cream and a soap bar.

3. The skin care method in accordance with claim 1, wherein:
   the skin care kit further includes a skin care regimen compliance report including the list of prohibited and allowed food items and a corresponding data input field for each food item in the list of prohibited and allowed food items.

4. The skin care method according to claim 3, further comprising indicating, by the user, an amount of each prohibited and allowed food item consumed by the user in the corresponding data input field of the skin care regimen compliance report.

5. The skin care method according to claim 4, further comprising determining, by the user, a level of compliance with the dietary skin care regimen, wherein a total number of servings of prohibited food items and allowed food items consumed by the user determines the user's level of compliance and the level of compliance is at least one of a high level, a moderate level, and a non-compliant level.

6. The skin care method according to claim 4, wherein the skin care kit further includes instructions for the user to follow a skin care lifestyle regimen and for the user to perform at least one of a plurality of lifestyle activities, the plurality of lifestyle activities including:
   drinking, by the user, a predetermined amount of water each day;
   exercising, by the user, a predetermined amount of time each day; and
   consuming, by the user, meals prior to a predetermined time of the day.

7. The skin care method according to claim 6, wherein the plurality of lifestyle activities further includes:
   drinking, by the user, forty-eight ounces of water each day;
   exercising, by the user, thirty minutes each day; and
   consuming, by the user, meals prior to 8 P.M.

8. The skin care method according to claim 7, further comprising determining, by the user, a level of compliance with the dietary and lifestyle skin care regimen, wherein a total number of serving of prohibited and allowed food items consumed by the user and a total amount of time in which the user performs the plurality of lifestyle activities determines the user's level of compliance and the level of compliance is at least one of a high level, a moderate level, and a non-compliant level.

9. The skin care method according to claim 3, wherein the skin care regimen compliance report is configured to be displayed on a computer display and configured to allow the user to input data into the data input fields via a user input device.

10. The skin care method according to claim 1, wherein the skin cleanser is soap bar comprising chamomile.

11. The skin care method according to claim 10, wherein the soap bar further comprises aloe vera.

12. The skin care method according to claim 1, wherein the skin cleanser comprises coconut oil.

13. The skin care method according to claim 1, wherein the skin care kit further includes a coaching subscription form that allows the user to obtain a subscription that gives the user access to a care center for a period of time, the care center including at least one operator trained to answer questions about the dietary skin care regimen.

14. The skin care method according to claim 13, further comprising accessing, by the user, a care center operator by one of calling the care center and logging on to the care center website.

15. A skin care method comprising the steps of:
obtaining, by a user, a skin care kit comprising:
a dietary supplement comprising an effective amount of thiamine, riboflavin, niacin, vitamin B6, vitamin B12, pantothenic acid, choline bitartrate, di-methionine, desiccated liver concentrate, and inositol;
a moisturizing cleansing cream;
a soap bar including chamomile;
instructions for following a dietary skin care regimen including:
instructions to not consume a food item from a list of prohibited food items, the list of prohibited food items including:
red meat;
chocolate;
an egg;
a confection;
an alcoholic beverage;
shellfish;
a tomato; and
a fried food item; and
instructions to consume foods from a list of allowed food items, the list of allowed food items including:
chicken;
turkey;
non-fried fish;
a vegetable;
a fruit other than a tomato; and
salad dressing in a form of olive oil;
a skin care regimen compliance report including the list of prohibited and allowed food items and a corresponding data input field for each food item in the list of prohibited and allowed food items; and
reading and following, by the user, instructions for the dietary skin care regimen;
consuming, by the user, a single serving of the dietary supplement each day; and
cleansing, by the user, the user's skin using the cleansing cream and soap bar each day.

16. The skin care method according to claim 15, further comprising:
inputting, by the user, data into data input fields via a user input device, wherein the skin care regimen compliance report is configured to be displayed on a computer display.

17. The skin care method according to claim 15, further comprising reading and following, by the user, instructions for a skin care lifestyle regimen including instructions for the user to perform at least one of a plurality of lifestyle activities, the plurality of lifestyle activities including:
drinking, by the user, a predetermined amount of water each day;
exercising, by the user, a predetermined amount of time each day; and
consuming, by the user, meals prior to a predetermined time of the day.

18. The skin care method according to claim 15, further comprising reading and following, by the user, instructions for a skin care lifestyle regimen including instructions for the user to perform at least one of a plurality of lifestyle activities, the plurality of lifestyle activities including:
drinking, by the user,, by the user, forty-eight ounces of water each day;
exercising, by the user, thirty minutes each day; and
consuming, by the user, meals prior to 8 P.M.

19. The skin care method in accordance with claim 15, wherein:
the skin care kit further includes instructions for completing the skin care regimen compliance report including instructions to indicate an amount of each prohibited and allowed food item consumed by a user in the corresponding date input field.

* * * * *